US008864707B1

(12) United States Patent
Vitello

(10) Patent No.: US 8,864,707 B1
(45) Date of Patent: Oct. 21, 2014

(54) TAMPER INDICATING CLOSURE ASSEMBLY

(75) Inventor: Jonathan Vitello, Fort Lauderdale, FL (US)

(73) Assignee: Medical Device Engineering, LLC., Pompano Beach, FL (US)

(*) Notice: Subject to any disclaimer, the term of this patent is extended or adjusted under 35 U.S.C. 154(b) by 180 days.

(21) Appl. No.: 13/310,385

(22) Filed: Dec. 2, 2011

Related U.S. Application Data

(60) Provisional application No. 61/419,508, filed on Dec. 3, 2010, provisional application No. 61/462,097, filed on Jan. 28, 2011.

(51) Int. Cl.
A61M 5/00 (2006.01)

(52) U.S. Cl.
USPC .......................................................... 604/111

(58) Field of Classification Search
USPC .......................................................... 604/111
See application file for complete search history.

(56) References Cited

U.S. PATENT DOCUMENTS

| | | | |
|---|---|---|---|
| 3,245,567 A | 4/1966 | Knight | |
| 3,747,751 A | 7/1973 | Miller et al. | |
| 4,216,872 A | 8/1980 | Bean | |
| 4,313,539 A | 2/1982 | Raines | |
| 4,420,085 A | 12/1983 | Wilson et al. | |
| 4,571,242 A | 2/1986 | Klein et al. | |
| 4,667,837 A | 5/1987 | Vitello et al. | |
| 4,726,483 A | 2/1988 | Drozd | |
| 4,832,695 A | 5/1989 | Rosenberg et al. | |
| 4,844,906 A | 7/1989 | Hermelin et al. | |
| 5,009,323 A | 4/1991 | Montgomery et al. | |
| 5,135,496 A | 8/1992 | Vetter et al. | |
| 5,165,560 A | 11/1992 | Ennis, III et al. | |
| 5,328,474 A | 7/1994 | Raines | |
| 5,458,580 A | 10/1995 | Hajishoreh | |
| 5,558,648 A | 9/1996 | Shields | |
| 5,624,402 A | 4/1997 | Imbert | |
| 5,785,691 A | 7/1998 | Vetter et al. | |
| 5,807,343 A | 9/1998 | Tucker et al. | |
| 5,883,806 A | 3/1999 | Meador et al. | |
| 6,000,548 A | 12/1999 | Tsals | |
| 6,027,482 A | 2/2000 | Imbert | |
| 6,068,614 A | 5/2000 | Kimber et al. | |
| 6,126,640 A | 10/2000 | Tucker et al. | |
| 6,190,364 B1 | 2/2001 | Imbert | |
| 6,193,688 B1 | 2/2001 | Balestracci et al. | |
| 6,196,998 B1 | 3/2001 | Jansen et al. | |
| 6,280,418 B1 | 8/2001 | Reinhard et al. | |
| 6,394,983 B1 | 5/2002 | Mayoral et al. | |
| 6,485,460 B2 | 11/2002 | Eakins et al. | |
| 6,520,935 B1 | 2/2003 | Jansen et al. | |

(Continued)

Primary Examiner — Jason Flick
(74) Attorney, Agent, or Firm — Malloy & Malloy, P.L.

(57) ABSTRACT

A closure assembly structured for use with a female luer connector and operative to indicate an accomplished or attempted tampering thereof. A connector cover is movably and removably disposed within a housing and includes an interior chamber disposed and structured to receive an access port of the female connector. An indicator member is removably connected to an interior of the housing in surrounding relation to the connector cover and a drive assembly associated with both the connector cover and the housing is operable to concurrently rotate and axially advance the interior chamber into enclosing relation to the access port. Attempted removal of the housing from the female connector, such as by an applied axial force to the housing, will detach the indicated member from the housing and dispose it in a visually observable position surrounding the connector cover, thereby indicating attempted access.

22 Claims, 7 Drawing Sheets

(56) References Cited

U.S. PATENT DOCUMENTS

| | | |
|---|---|---|
| 6,565,529 B1 | 5/2003 | Kimber et al. |
| 6,581,792 B1 | 6/2003 | Limanjaya |
| 6,585,691 B1 | 7/2003 | Vitello |
| 6,726,652 B2 | 4/2004 | Eakins et al. |
| 6,821,268 B2 | 11/2004 | Balestracci |
| 6,921,383 B2 * | 7/2005 | Vitello .................. 604/111 |
| 6,942,643 B2 | 9/2005 | Eakins et al. |
| 7,141,286 B1 | 11/2006 | Kessler et al. |
| 7,374,555 B2 | 5/2008 | Heinz et al. |
| 7,425,208 B1 | 9/2008 | Vitello |
| 7,588,563 B2 | 9/2009 | Guala |
| 7,632,244 B2 | 12/2009 | Buehler et al. |
| 7,641,636 B2 | 1/2010 | Moesli et al. |
| 7,735,664 B1 | 6/2010 | Peters et al. |
| 7,762,988 B1 | 7/2010 | Vitello |
| 8,348,895 B1 | 1/2013 | Vitello |
| 8,353,869 B2 | 1/2013 | Ranalletta et al. |
| 8,616,413 B2 | 12/2013 | Koyama |
| 2002/0133119 A1 | 9/2002 | Eakins et al. |
| 2004/0064095 A1 | 4/2004 | Vitello |
| 2004/0116858 A1 | 6/2004 | Heinz et al. |
| 2004/0225258 A1 | 11/2004 | Balestracci |
| 2011/0044850 A1 * | 2/2011 | Solomon et al. ................ 422/28 |
| 2012/0064515 A2 | 3/2012 | Knapp et al. |

* cited by examiner

TAMPER INDICATING CLOSURE ASSEMBLY

CLAIM OF PRIORITY

The present Non-Provisional patent application claims priority pursuant to 35 U.S.C. Section 119(e) to prior filed Provisional patent application, namely, that having Ser. No. 61/419,508 filed on Dec. 3, 2010, as well as to another prior filed Provisional application, namely, that having Ser. No. 61/462,097 filed on Jan. 28, 2011, the contents of which are both incorporated herein by reference in their entireties.

BACKGROUND OF THE INVENTION

1. Field of the Invention

This invention is directed to a closure assembly for use on a female luer connector or other generally similar connector of the type used with intravenous (IV) administration assemblies for the dispensing IV fluid and/or the adding of medicine or other agents to the IV container for dispensing. The closure assembly is structured to restrict unauthorized access to the female luer connector and further, to provide an obvious indication of attempted access to or other efforts to tamper with the female connector and/or contents of the IV reservoir.

2. Description of the Related Art

In the medical field, it is a relatively common procedure to administer fluids to a patient by intravenous (IV) infusion. A variety of IV assemblies are known and are useful in the treatment of a number of medical conditions, in that a variety of fluids and/or medicines can be administered to a patient utilizing such assemblies over a prescribed period of time and in controlled amounts. In use, a conventional IV administration assembly typically includes a reservoir or container, in the form of a bottle or more commonly, a flexible material bag, suspended on a pole or like support structure located substantially adjacent to the patient being treated, typically in an elevated relation thereto. In addition, the IV fluid flows from the supported and elevated IV bag to the patient by means of elongated, flexible tubing connected at a proximal end to the IV bag and at the other distal end, connected intravenously to the patient by way of a catheter or like structure. The IV delivery tube is also structured to connect at one end to or be interconnected with an appropriate connector, often having somewhat of a "Y" shape, that is associated with the IV assembly and in fluid communication with either the contents of the IV bag or alternatively, with the catheter in use on the patient for intravenous administration of fluids and medicines.

One such connector may be in the form of a female connector attached to the IV bag or other container and disposed in fluid communication with the contents thereof. An appropriate female connector may be in the form of a female luer connector which at least partially defines, along with a male luer connector, a "luer lock" connector assembly, as is well known in the medical profession. The male luer connector is secured to the IV delivery tubing, such as at the proximal end, and is specifically structured to be attached to the female luer connector in a manner which establishes fluid communication with contents of the IV container, and facilitates a flow of the IV fluid from the IV container through the connected male and female luer connectors. As a result, fluid flow between the patient and the interior of the IV bag is established. As is also well known, various types of valves and/or flow regulating devices may be operatively associated with the IV assembly to regulate the amount of fluid or rate of fluid delivery to the patient during the administration procedure.

In addition, known IV containers or reservoirs may incorporate an additional female luer connector or other female type connector which are disposed in fluid communication with the IV delivery tubing, such as but not limited to at the IV bag. This additional female luer connector is provided to administer additional liquid agents, such as pain medication, antibiotics, and/or other medicinal compositions, to the IV fluid being delivered to the patient. However, such an additional female luer connector may remain unused or may be accessed at a time subsequent to the initiation of the IV fluid administration, such as when additional medication or another composition is required or prescribed.

In periods of non-use, it is important to maintain a female luer connector in a closed and fluid sealed condition in order to maintain sterility, and also, the integrity of the IV fluid prior to use. This is also important in order to restrict unauthorized access to the IV fluid and even to the female luer connector. Therefore, there is a need in the medical field for an efficient, effective and easily applied closure assembly that would be capable of closing and sealing a female connector during periods of its non-use. If any such closure assembly were developed, it should also be structured to provide a clear visual indication whenever there has been tampering or other attempted access to the female luer connector and/or contents of the IV container. Moreover, if any such closure assembly were developed, it should also be structured for efficient attachment to the female luer connector so as to prevent re-attachment to the female connector, once unauthorized access has been attempted or accomplished. If any such closure assembly were developed, it should also be capable of being removed from the female connector in a manner which provides the aforementioned visual or other appropriate indication of complete, partial or other attempted access to the female luer connector.

Finally, the structural components as well as the operational characteristics of any such closure assembly developed should ideally also provide a sufficient degree of reliability relating to the secure closing and sealing of the female connector of the IV container, while restricting access and clearly indicating when access thereto has occurred or been attempted.

SUMMARY OF THE INVENTION

The present invention is intended to present a solution to these needs which remain in this field of art and as such, is directed to a closure assembly that is specifically, but not exclusively, structured for the closing and/or sealing of a female connector such as, but not limited to, a female luer connector having an access port or flow port. The present inventive closure assembly is also preferably structured to indicate if there has been any tampering with the closure assembly and associated female connector. Such female connectors are commonly used, as has been described previously herein, along with a cooperatively structured male luer connector, as part of a "luer lock" connector assembly found on and/or used in combination with a variety of medical devices, including intravenous (IV) dispensing or administration assemblies. As such, the female luer connector or another generally similar type of connector is disposed and structured to facilitate the dispensing of the IV fluid from the IV container and/or for the addition of medicine or other agents to the IV liquid prior to or concurrent with its administration intravenously to a patient. Moreover, the female luer connector, as described above, facilitates the addition of medicine or other compositions by means of a pre-loaded syringe which does not use a needle. Specifically, and as has become relatively commonplace following awareness of the AIDS virus and how AIDS is transmitted, needle-less syringes may be pre-loaded with a medicine or substance to be given to a patient. These needle-less syringes typically include an elongated, male-type of discharge nozzle that is dimensioned and configured to be received within the access port of a female luer connector and thereby, eliminate the need for an actual needle to be attached to the syringe.

Accordingly, and in order to restrict or at least provide a clear indication of attempted access to the female connector and the contents of the IV container, the present invention is directed to a tamper evident closure assembly, which is connected in closing and possibly fluid sealing relation to the female connector. The structure of the closure assembly restricts its removal from the female luer connector without providing an obvious indication that tampering or attempted access has occurred. Also, once removed from the female connector, the tamper evident closure assembly of the present invention is ideally structured so that it cannot be re-attached, in an attempt to hide an unauthorized attempted access.

Turning now to the structural and operative features of the present inventive closure assembly, they include a housing that has an at least partially hollow interior dimensioned and structured to enclose and at least partially retain a connector cover therein. In addition, the housing includes a closed end portion and an oppositely disposed open end. The open end of the housing is of sufficient dimension to at least partially receive a portion of the female connector, including the access port, there through into an interior chamber of the connector cover. The connector cover is movably and removably disposed within the housing and is structured to be threaded or otherwise appropriately connected to the female connector concurrently to the closure assembly being attached to the female connector. As such, the interior surface of the interior chamber is structured to connect with the exterior surface of the female connector in a manner which serves to advance the interior chamber into enclosing relation with the access port of the female connector.

In addition, an indicator member is fixedly but preferably removably connected to the housing and is disposed on the interior thereof in at least partially surrounding relation to a correspondingly disposed part of the connector cover. At least one, but possibly a plurality of frangible members, detachably interconnects the indicator member to the interior surface of the housing. The indicator member is thereby initially fixed to, but detachable from, the interior of the housing. Moreover, when fixed to the housing the indicator member and the aforementioned closed end portion of the housing are cooperatively disposed to movably retain the connector cover within the housing in a position which facilitates the advancement and or movement of the connector cover into a connected relation with the female luer connector.

As set forth above, the various preferred embodiments of the closure assembly of the present invention are specifically, but not exclusively, structured to cover, enclose and possibly seal the access port of the female connector. Therefore, structural components associated with the connector cover include the aforementioned interior chamber which may be more specifically defined by an interior portion comprising a surrounding, interior surface. As also set forth above, the surrounding interior surface is cooperatively structured with the exterior portions of the female connector to accomplish an axial advancement of the connector cover and the interior chamber into a receiving, and at least partially enclosing relation with the access port of the female connector, concurrently to a rotation of the connector cover. Moreover, the interior chamber includes an open end and an oppositely disposed closed end disposed in interconnecting relation by the surrounding interior surface of the interior chamber. The open end and the closed end of the connector cover are disposed a sufficiently spaced distance from one another to receive and enclose at least a majority of the access port, and possibly at least a portion of the remainder of the female connector within the interior chamber.

Cooperative structuring of the housing includes the open end thereof disposed opposite to the closed end portion, wherein the housing and the open end are sufficiently dimensioned and configured to receive and surround a remaining portion of the female connector other than the access port. Further, the connector cover and the interior chamber are spaced inwardly from the open end of the housing and are disposed to at least partially enclose the access port concurrently to the housing surrounding at least a portion of the remainder of the female connector.

Additional structural and operative details of the present inventive closure assembly facilitate its attachment to a female connector in enclosing and/or flow restricting engagement with the access port of the female connector. Further, once the closure assembly is attached to the female connector it cannot be removed there-from without providing a clear indication of tampering and/or attempted access to the female connector and the contents of the IV container or other device with which the female connector is associated. Also, once removed from the female connector, the closure assembly cannot be re-attached thereto in an operative manner.

The closure assembly of the present invention preferably also includes a drive assembly. Moreover, one or more preferred embodiments include the drive assembly comprising a first drive segment and a second drive segment, wherein the first drive segment is disposed on the interior of the housing and mounted on or connected to the interior of the closed end portion of the housing. The second drive segment is operatively disposed relative to the first drive segment by being connected to or mounted on a portion of the connector cover which is disposed in confronting relation and/or engagement with the interior surface of the closed end portion. In at least one preferred embodiment of the present invention, the first and second drive segments each include what may be referred to as a rotational type "ramp and cliff" drive structure. In addition, the ramp and cliff drive structures of each of the first and second drive segments may be mirror images of one another and substantially reversely oriented. As a result, interaction between the confronting surfaces of the first and second drive segments during rotation of the housing and the closed end portion connected thereto, in a single predetermined direction, will cause a rotation of the connector cover. Concurrent to its rotation, the connector cover and the interior chamber will be advanced axially as the connector cover becomes attached to the female connector. The connector cover will thereby be disposed into the aforementioned covering, enclosing, surrounding and/or flow restricting relation to the access port of the female connector. Therefore, the drive assembly of the present invention may be described as a "one way drive assembly" due to the ability to rotate the connector cover and in turn cause its axial advancement into flow restricting engagement with the access port of the female connector. As set forth herein rotation of the housing in a predetermined, single predetermined direction will result in the rotation of the connector cover.

More specifically, the rotational type ramp and cliff structures formed on each of the first and second drive segments provide concurrent rotation of the housing and the connector cover, when the housing is rotated in the one, predetermined direction. Rotation of the housing in a direction opposite from the one, predetermined direction will result in the ramp and cliff drive structures of the first and second drive segments being disposed out of driving relation to one another and a "slippage" or relative sliding movement there between. Therefore, it should be apparent that the connector cover and interior chamber are rotationally mounted within the interior of the housing. Due to the cooperative structuring of the first and second drive segments, the interior chamber will be disposed in enclosing relation and possibly flow restricting relation to the access port of the female connector as the housing is rotated in the one, predetermined direction. However, rotation of the housing in the opposite direction will not accomplish a removal of the connector cover from its connection with the female connector or the removal of the access port of the female connector from within the interior chamber, and therefore, will not serve to remove the housing of the closure assembly from the female connector.

Removal of the housing from the female connector, in order to access the connector cover and eventually the contents of the IV container, can be effectively accomplished by exerting an appropriate force such as, but not limited to, an axially directed or "pulling" force on the housing. Such force, in order to be sufficient to remove the housing from the female connector, must be adequate to detach the indicator member from the interior of the housing. Such detachment will be a result of the axial or other appropriately directed force being exerted on the housing and being sufficient to break or rupture the one or more frangible members which connect the indicator member to the interior of the housing, as set forth above. When the housing is detached, the indicator member, preferably in the form of a color-coded ring or like structure, will remain and be readily observable in surrounding relation or other direct association with the now exposed connector cover. As such, the connector cover will remain connected to the female connector. Therefore, the presence of the indicator member on the connector cover will be a clear indication of tampering or attempted access to the contents of the IV container and/or female connector and will be capable of being easily and immediately observed.

Therefore, the one or more preferred embodiments of the closure assembly of the present invention provide a sufficient and reliable structure for closing and possibly sealing a female luer connector or other female connector of the type which may be associated with an IV container or other device. The tamper evident closure assembly is further structured to provide a clear indication of tampering or attempted access to the female connector and other devices with which the female connector may be associated.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 2:
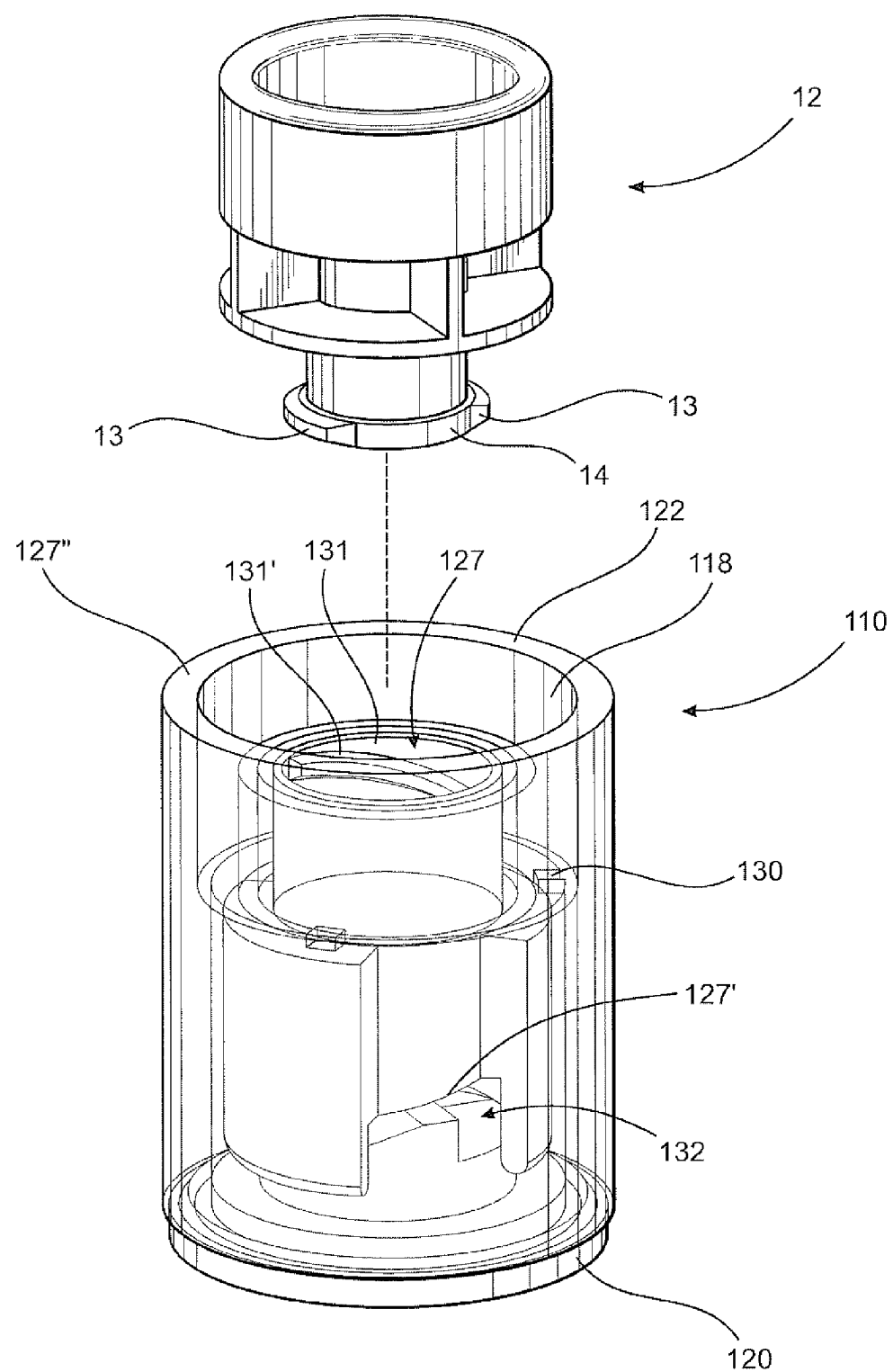
FIG. 2 is an exploded, perspective view of the closure assembly of the present invention also disclosing interior portions of thereof, and in a position for attachment to a female connector, such as a female luer connector of the type used with IV dispensing assemblies.

As represented in the accompanying drawings, the present invention is directed to a closure assembly, generally indicated as 110, which is preferably a tamper evident closure assembly. The closure assembly 110 is structured to enclose and will preferably provide a fluid seal with a female connector, generally indicated as 12, as is perhaps best shown in FIG. 2. In at least one preferred embodiment, the female connector 12 is more specifically defined and structured as a female luer connector including, as shown in FIG. 2, an interior port or access port 14 structured for the passage of fluid therethrough from a IV container or IV bag, or other reservoir with which the female luer connector 12 is associated. By way of example, a female luer connector or other female type connector may be connected to and/or directly associated with an intravenous (IV) dispensing assembly (not shown) of the type commonly used to administer fluid to a patient over a prescribed period of time, as has been described previously herein. As such, elongated flexible tubing having a male luer connector secured to one end may be attached to the female connector 12, shown in FIG. 2, by insertion within the access port 14 in order to dispense the fluid contents from the IV container to the patient. In addition, the female luer connector 12 may also be utilized to add an additional agent or composition to the fluid being dispensed from the IV container. In such situations, a preloaded syringe having an elongated nozzle may be inserted into the access port 14 of the female connector 12.

Accordingly, it is desirable to maintain the female connector 12 closed and/or sealed when not being used in order to maintain sterility and to prevent inadvertent and/or unauthorized access to the contents of the IV container, with which the female connector is associated. Therefore, at least one embodiment of the closure assembly 110 includes structural and operative features which accomplish a closed and preferably, fluid sealing of the female connector 12. Further, the closure assembly 110 is structured to provide a clear indication of tampering or attempted access to the female connector 12 and the contents of the IV container with which it is associated.

Figure 1:
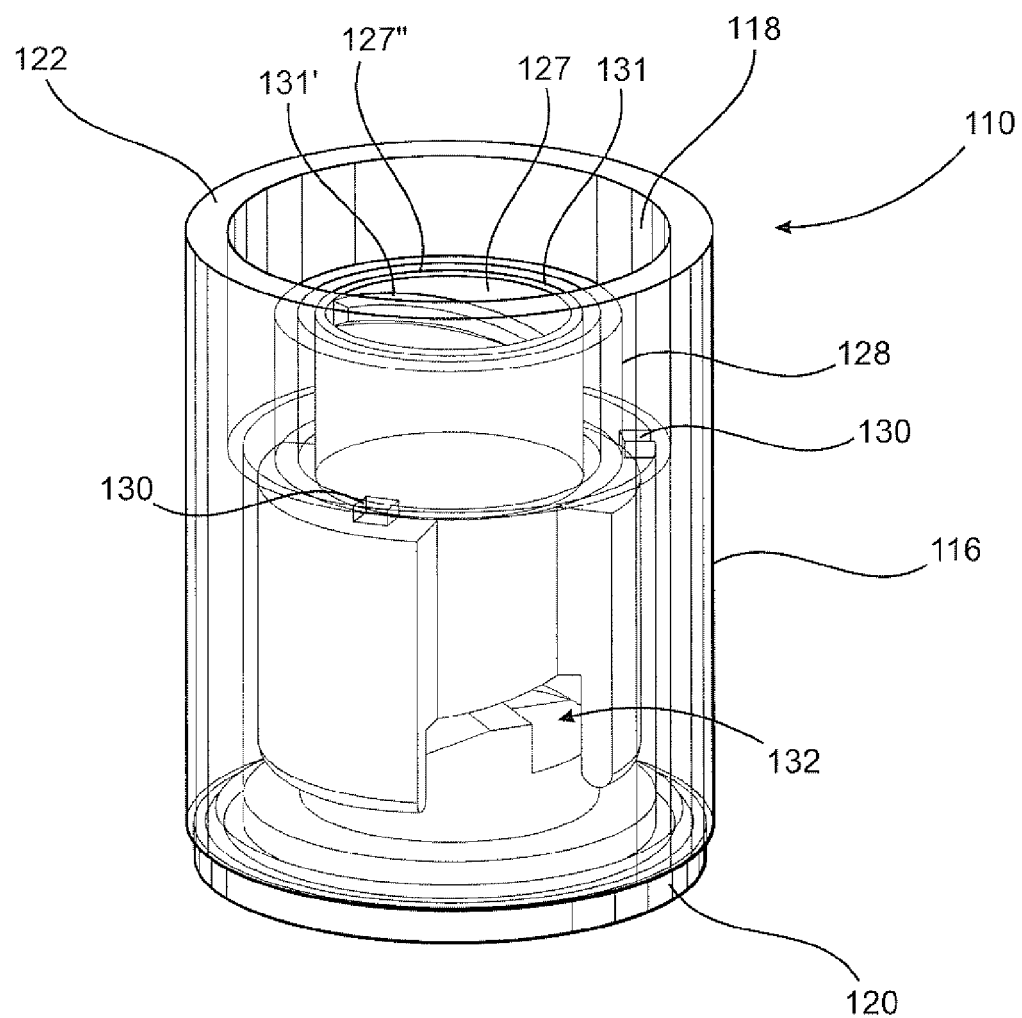
FIG. 1 is a perspective view of the closure assembly of the present invention disclosing interior portions of thereof.
Figure 3:
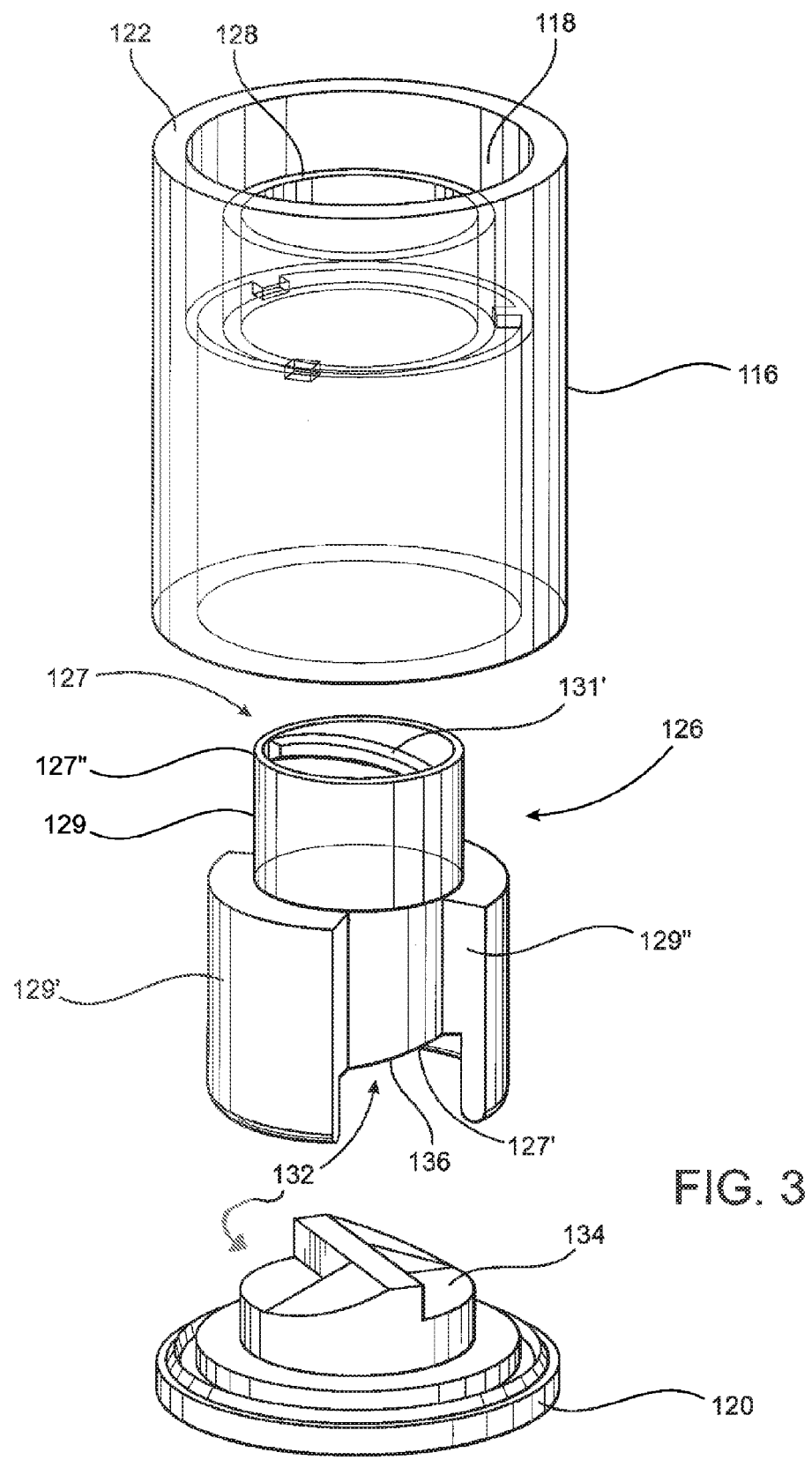
FIG. 3 is an exploded, perspective view in schematic form of the various components of the embodiment of the closure assembly of FIGS. 1 and 2.

As represented in FIGS. 1-3, the tamper evident closure assembly 110 includes a housing 116 having an at least partially hollow interior 118 of sufficient dimension to contain additional structural components that are operatively associated with the closure assembly 110. Also, and as is best shown in FIG. 1, the housing 116 includes a closed end portion 120 and an oppositely disposed open end 122. The open end 122 is sufficiently dimensioned and configured to allow at least a portion of the female luer connector 12 to pass therethough. Therefore, when the closure assembly 110 is operatively connected to the female connector 12, at least a portion of the female connector 12, including the access port 14, is at least partially disposed within the interior 118 of the housing 116 by passing through the open end 122.

FIG. 2 collectively and schematically represents the relative orientations of the closure assembly 110, including housing 116, and the female luer connector 12, immediately prior to interconnection therebetween. In addition, FIGS. 1-3 provide schematic representations of the different structural components of the closure assembly 110 and the operative features associated therewith. Moreover, as represented in FIG. 3 the closure assembly 110 is represented in an unassembled state for purposes of helping to illustrate most components associated with the present invention. It is emphasized that the closure assembly 110 will be fully assembled, as disclosed in FIGS. 1 and 2, prior to connection to the female luer connector 12.

The housing 116 includes the closed end portion 120 being integrally or otherwise fixedly connected to one end thereof, including by adhesive, welding or even sonic welding, with the closed end 120 being oppositely disposed to the open end 122. The at least partially hollow interior 118 of the housing 116 is dimensioned and configured to receive a connector cover, generally indicated as 126 therein, as is perhaps best illustrated in FIG. 3, but also in FIGS. 4 and 5. Further, the closure assembly 110 preferably includes an indicator member 128, perhaps best shown in FIG. 3 that ideally includes an annular configuration and having an interior dimension sufficient to receive at least a portion of the connector cover 126 therethrough, as also represented in FIGS. 1 and 2. The indicator member 128 is fixedly but detachably secured to the interior surface of the housing 116 by at least one but possibly a plurality of frangible members 130, shown in FIGS. 1 and 2. The one or more frangible members 130 are fixedly but detachably secured in interconnecting relation between the interior surface of the housing 116 and the exterior surface of the indicator member 128. Moreover, the one or more frangible members 130 are specifically structured to break or rupture and thereby, be detached from their initially interconnecting relation between the housing 116 and indicator member 128, upon a sufficient force, such as an axial force, being applied to the housing 116, as set forth in greater detail hereinafter.

Therefore, the indicator member 128 is initially disposed in fixed interconnection on the interior of the housing 116. In contrast, the connector cover 126 is movably disposed within and removable from the interior 118 of the housing 116. More specifically, the connector cover 126 is movably and removably disposed in a captured or retained position between the fixedly connected closed end portion 120 and the initially fixed indicator member 128. As a result, the connector cover 126 is disposed and dimensioned to move at least rotationally within the interior 118 between the closed end portion 120 and the indicator member 128. Such movement of the connector cover 126 can be accomplished, at least initially, before connection of the closure assembly 110 to the female connector 12 as shown in FIG. 2. As will be more fully explained, the rotational movement of the connector cover 126, within the interior 118 of the housing 116, serves to accomplish the connection of the connector cover 126 and the closure assembly 110 to the female connector 12. As a result, the connector cover 126 will be axially advanced or positioned into the closing and possibly fluid sealing relation to the access port 14 of the female luer connector 12, concurrently to the rotation of the closure assembly 110 and the connector cover 126 by interaction and operation of a drive assembly, generally indicated as 132, in FIGS. 1-3.

Figure 4:
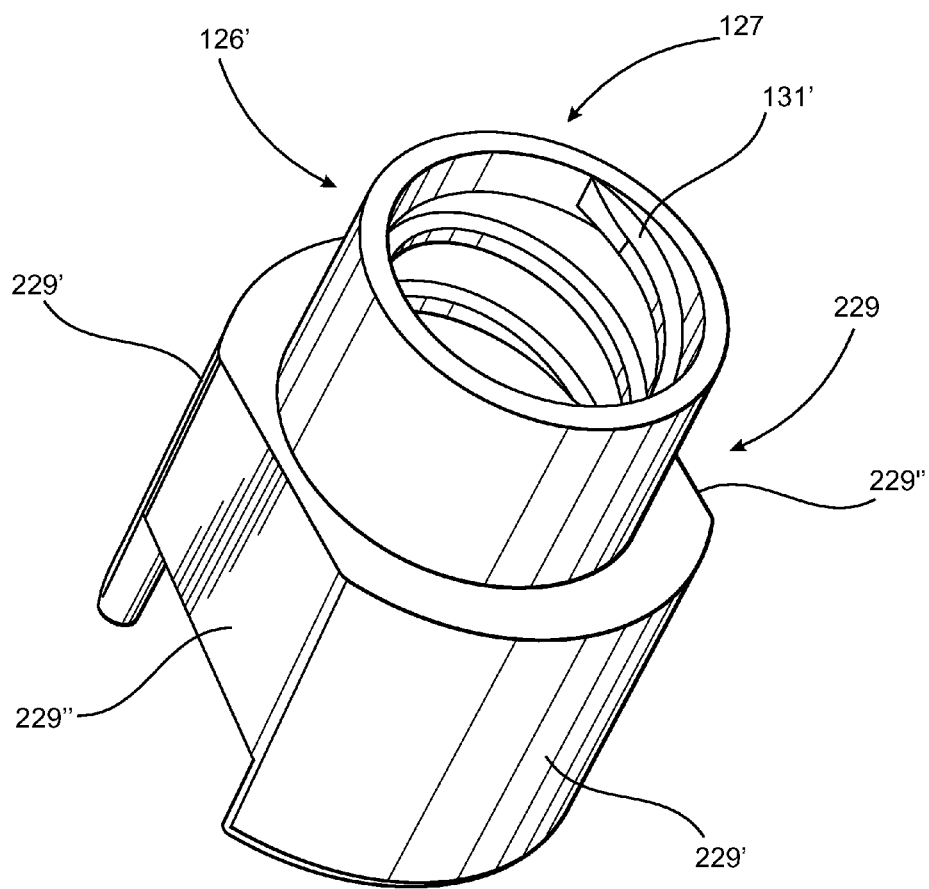
FIG. 4 is a perspective view of another embodiment of a component of the closure assembly of the present invention.

The intended enclosing, surrounding and possibly fluid sealing connection and/or disposition of the closure assembly 110 with the female connector 12 are accomplished by the connector cover 126 including an interior chamber 127, as is perhaps best illustrated in FIGS. 3 and 4. Moreover, in at least one preferred embodiment the interior chamber 127 is dimensioned and configured to receive at least the access port 14 of the female luer connector 12 therein. The interior chamber 127 includes a closed end and an oppositely disposed open end 127' and 127" respectively. An interior surface portion 131, best shown in FIGS. 1 and 2 extends between the closed end 127' and the open end 127", which are sufficiently spaced from one another to receive and enclose at least a portion of the female connector 12, specifically including the access port 14. Moreover, the interior chamber 127 may be further dimensioned, configured and structured to provide a fluid tight seal with regard to the access port 14.

With reference now to FIG. 3, yet additional features of the connector cover 126 preferably include a casing 129 disposed in surrounding relation to the interior chamber 127. Relative dimensions and positions of the casing 129 and the interior chamber 127 facilitate the insertion of the access port 14 of the female connector 12, when the closure assembly 110 is connected to the female connector 12 in the intended manner. The casing 129 also includes an exterior structure preferably in the form of segmented portions 129'.

As is perhaps best represented in FIG. 3, the casing 129 also includes an exterior structure which may include segmented portions 129' separated by spaces 129" which are disposed on opposite sides of the casing 129. The dimension and disposition of the segmented portions 129' may facilitate a movable but secure positioning of the connector cover 126 on the interior 118 of the housing 116. Also, the configuration of the exterior of the casing 129, as collectively defined by the alternating segments 129' and spaces 129" may facilitate the gripping and manual rotation of the connector cover 126 relative to the female connector 12 by an individual, such as a nurse, whenever that is required. However, in the additional embodiment of FIG. 4, the connector cover is structurally modified and generally indicated as 126'. As shown in FIG. 4, the casing 229 includes an exterior structure that offers a smoother configuration with less sharp edges, so that manipulation, when needed, is facilitated, and thus, the casing 229 comprises oppositely disposed curved segments 229' separated from one another by oppositely disposed substantially flat segments 229". Therefore, in the embodiment of FIG. 4, the spaces 129" have been eliminated and replaced by the flat segments 229". As a result, the configuration of the exterior of the casing 229, as collectively defined by the alternating curved segments 229' and flat segments 229" may further facilitate the gripping and manual rotation of the connector cover 126' relative to the female connector 12 by an individual, when such is required.

The connector cover 126 is also cooperatively structured with the female connector 12 to accomplish a stable connection therewith. More specifically, attachment of the connector cover 126 in the surrounding, enclosing relation to the access port 14 of the female connector 12 is preferably accomplished by a threaded interconnection. Such cooperative structuring comprises the female connector 12 including outwardly extending ears, tabs or like projections 13, as is perhaps best shown in FIG. 2. In cooperation therewith, a threaded portion or portions 131' of the connector cover 126 (as perhaps best shown in FIG. 4) are disposed on the interior surface 131 of the interior chamber 127 of the connector cover 126. The interior threaded portion or threaded surface 131' is/are disposed and structured to receive the protruding connecting ears 13 of the female connector 12 upon the aforementioned rotation of the connector cover 126 and housing 116 relative to the female connector 12. As indicated above, the rotation of the housing 116 in the predetermined one direction and the interaction of the projections 13 and threaded surface or portion(s) 131' will cause the axial movement of the connector cover 126 concurrent to the rotation of the connector cover 126 and housing 116, due to the operation of the drive assembly 132. The result will be a threaded engagement of the connecting ears 13 of the female connector 12 and the internally threaded portion or surface 131' of the interior chamber 127 of the connector cover 126. Moreover, threaded interaction of the ears 13 and the threaded portion 131' during concurrent rotation of the housing 116 and the connector cover 126 will facilitate the axial movement and placement of the interior chamber 127 into the receiving, enclosing, surrounding and possibly fluid sealing relation with the access port 14 of the female connector 12.

With reference now to FIG. 3, and as set forth above, attachment of the closure assembly 110 in a covering, enclosing engagement with the female connector 12 is facilitated by the operative and structural features of the drive assembly 132. As utilized, the drive assembly 132 may be more specifically described as a one way drive assembly and includes a first drive segment 134 that can be integrally or otherwise fixedly secured on or mounted to an interior of the closed end portion 120. The drive assembly 132 also includes a second drive segment 136 integrally or otherwise fixedly secured to an exterior of the closed end 127' or other portion of the connector cover 126, which is disposed in operative, interactive relation to the first drive segment 134. Each of the first and second drive segments 134 and 136 is cooperatively structured to define the aforementioned one way drive assembly by comprising a "ramp and cliff" drive structure configuration. More specifically, the ramp and cliff drive structures of each of the first and second drive segments 134 and 136 may comprise mirror image patterns, in relief of one another, as they are mounted on correspondingly disposed confronting surfaces of the closed end portion 120 and connector cover 126, respectively. As described, the closed end portion 120 is fixedly secured to the remainder of the housing 116 and rotates therewith, while the connector cover 126 is movable within the housing 116. When assembled, the first drive segment 134, movable with the closed end portion 120, is disposed in confronting relation with the second drive segment 136, which is movable with the connector cover 126.

Therefore, a rotation of the housing 116 in a single, predetermined direction will cause a driving engagement of the first drive segment 134 with the second drive segment 136 and a forced, concurrent rotation of the connector cover 126 and interior chamber 127, with the housing 116. Continued rotation of the housing 116 and the connector cover 126 in the same, single predetermined direction will result in a rotational and axial movement of the connector cover 126 and the interior chamber 127 into the receiving, enclosing, surrounding and possibly fluid flow restricting relation to the access port 14 of the female connector 12, as well as a threaded or other stable type connection of the connector cover 126 to the female connector 12. However, due to the structuring and relative orientations of the ramp and cliff structures of both the first and second drive members 134 and 136, rotation of the housing 116 in a direction opposite to the one, single, predetermined preferred direction, will result in a slippage or sliding of the first and second drive segments 134 and 136 relative to one another. Therefore, rotation of the housing in this opposite direction will not accomplish removal of the access port 14 of the female connector 12 from within the interior chamber 126 or removal of the housing 116 from the female connector 12.

As a result of the above, access to the access port 14 of the female connector 12 and accordingly, the contents of a reservoir with which the female connector 12 may be associated is primarily, if not exclusively, accomplished by a pulling, substantially axial force being applied to the housing 116, in a direction away from the female connector 12 to which it is attached. The degree of axial or other directional force applied to the housing 116, which allows it to be removed from the female connector 12, will be sufficient to cause a rupturing or breakage of the one or more frangible members 130. In turn, the indicator member 128 will be detached from the interior of the housing 116 and remain in surrounding relation to the exterior of the connector cover 126, which will still be threaded or otherwise connected to the female connector. Detachment of the housing 116 from the female connector 12 and the indicator member 128 will expose both the indicator member 128, and the still connected connector cover 126, and typically also the frangible members 130, resulting in a clear indication of tampering or attempted access to the female connector 12 and contents of the fluid reservoir with which it is associated. Further visual enhancement of attempted tampering may be accomplished by a color coding of the indicator member 128, thereby providing a clear visual indication with minimal observation that tampering or attempted access to the female luer connector 12 has occurred.

Figure 5:
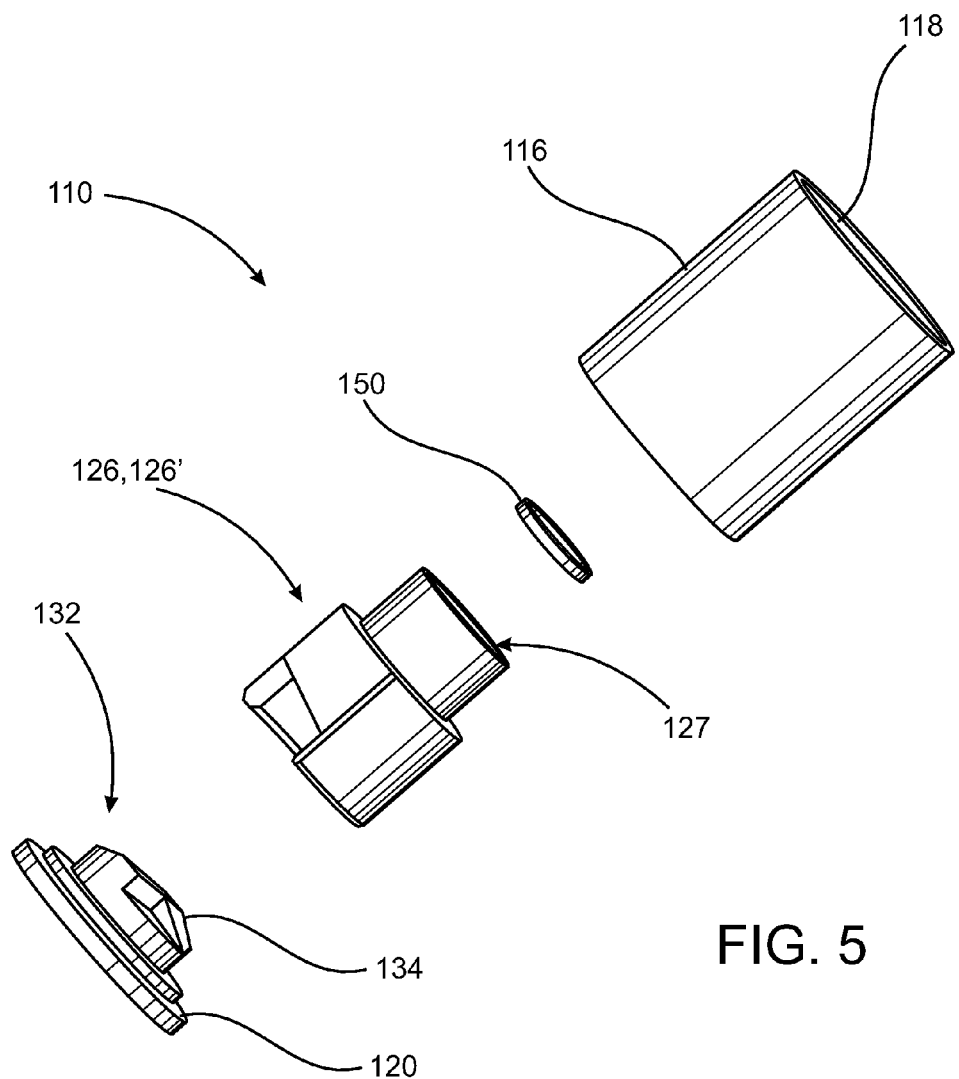
FIG. 5 is a perspective view in exploded form of yet another embodiment of the closure assembly of the present invention.

Yet another preferred embodiment of the present invention is represented in FIG. 5 and relates to the establishment and/or maintenance of a substantially sterile environment for the female connector 12, once the closure assembly 110 is attached thereto. More specifically, a disinfecting structure preferably, but not necessarily, in the form of a disinfecting pad 150 is added to the closure assembly 110 by inserting it into the interior chamber 127 of the cover structure 126 or 126'. Moreover, the pad 150 may be formed from foam or other appropriate material, which is at least partially impregnated with or otherwise contains a disinfecting agent. By way of example only, the pad 150 may be impregnated with alcohol, and impregnated to a level of close to or generally about 70% alcohol. It is emphasized that impregnating compositions other than alcohol may be used and the degree of impregnation may be more or less than the 70% set forth in the noted example. Also, the pad 150 may be formed of a variety of materials other than and/or in addition to foam. However, the different possible materials should include cooperative physical and operative characteristics which facilitate the use thereof with alcohol or other selected disinfectants. Also the dimension and configuration of the pad 150, which may be disk-shaped, will also be variably dependent at least on the size of the cover structure 126, 126', and should facilitate the placement and/or maintenance of the pad 150 in a position within the chamber 127 which facilitates the disinfecting of the access port 14 and/or other portions of the female connector 12. Accordingly, the pad 150 may be substantially fixed within the chamber 127, such as by a frictional engagement, double faced tape or adhesive securement with the interior portions of the chamber 127. Alternatively, the disinfecting pad may be positioned within the chamber 127 without being fixedly secured therein.

Figure 6:
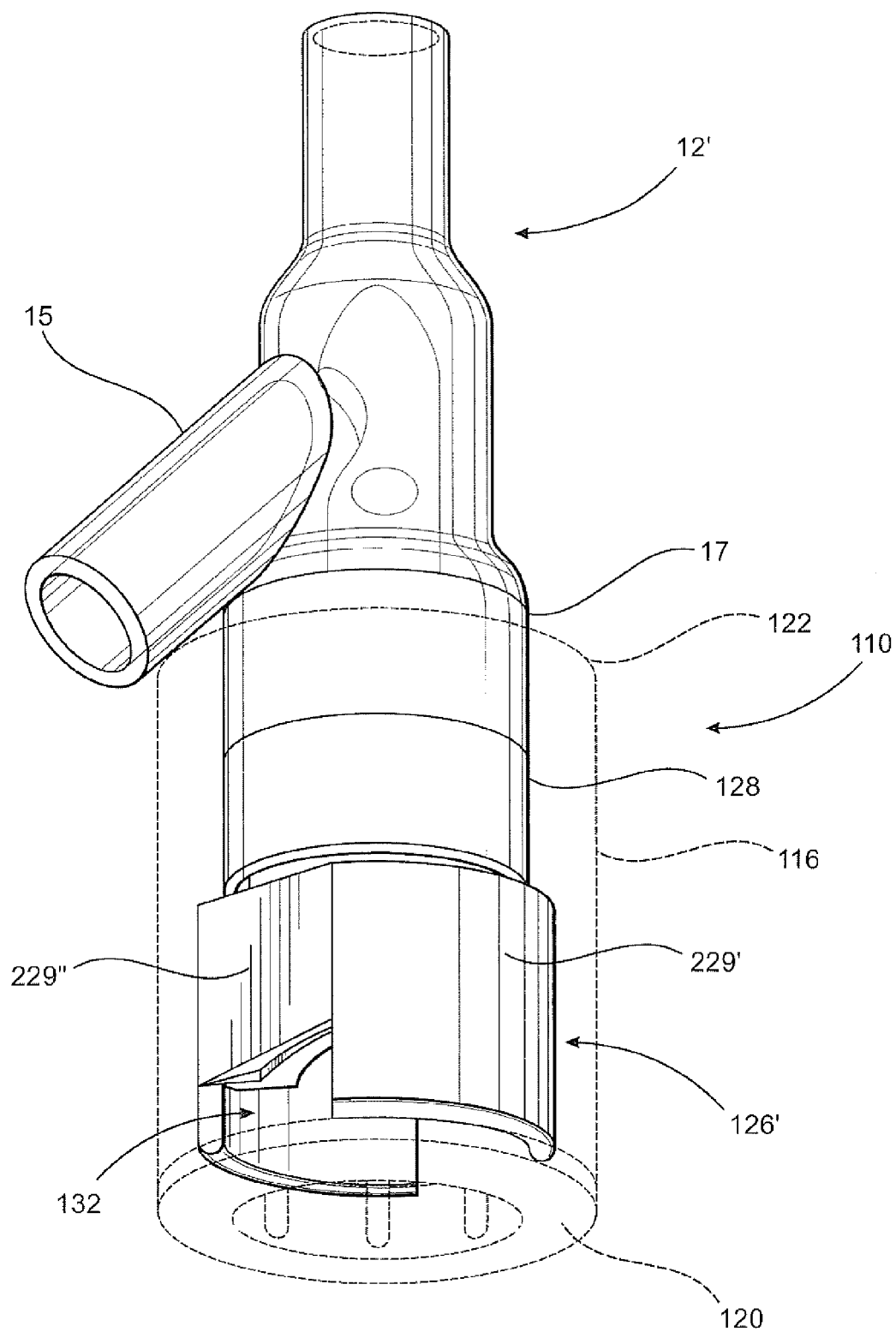
FIG. 6 is a perspective view in partial phantom of the closure assembly of the present invention connected in an operative position to a female connector.
Figure 7:
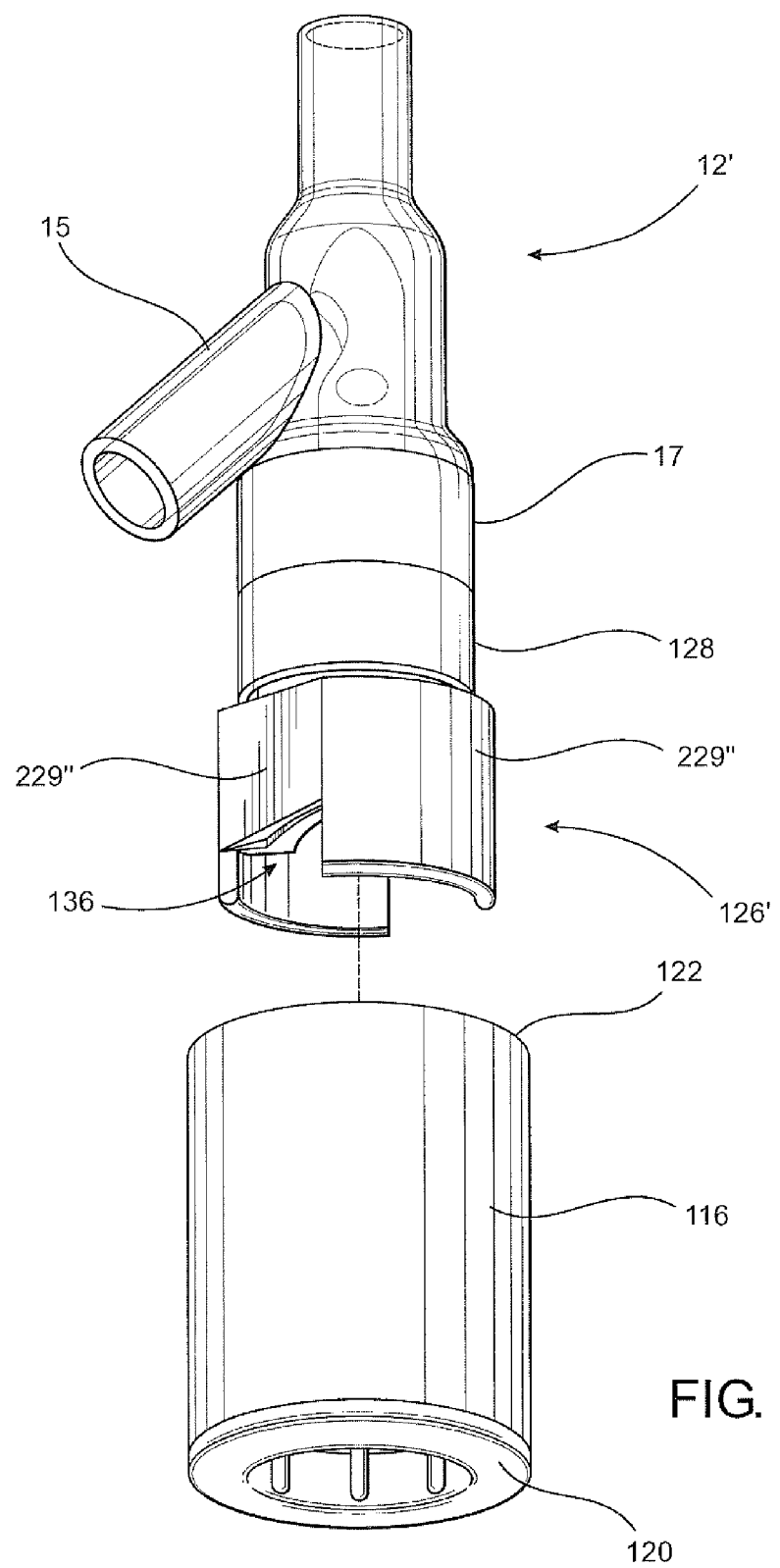
FIG. 7 is a perspective view in exploded form of the closure assembly of the embodiment of FIG. 6, wherein access to the female connector is attempted, resulting in a housing of the closure assembly having been removed, exposing an indicator member evidencing the attempted access.

The structural advantages and operational versatility of the closure assembly 110 are demonstrated in FIGS. 6 and 7. More specifically, FIG. 6 represents the closure assembly 110 connected to a generally "Y" shaped female connector 12' of the type that may be associated with IV tubing or an IV container or other medical equipment, which incorporates the use of a female connector specifically, but not exclusively, including a female luer connector. It should be further noted that the female connector 12' more accurately represents a connector of the type which is in use and/or commercially available as versus the schematic representation of the female connector 12 as disclosed in FIG. 2. As such, the female connector 12' may also include a supplementary access post 15 and an exterior cover 17 disposed in surrounding or enclosing relation to the access port 14, with the latter having been shown in FIG. 2.

Accordingly, once the closure assembly 110 is in the connected position of FIG. 6, the connector cover 126' will serve to close and/or seal the access port 14 due to the access port 14 being enclosed within the interior chamber 127 of the container closure 126'. Also, as set forth above, when in the operative, protective position of FIG. 6, the indicator member 128 will still be attached in a non-observable position within the interior 118 of the housing or sleeve 116. In contrast, and with primary reference to FIG. 7, when authorized or unauthorized access to the female connector 12' is attempted, a directional force will be exerted on the housing 116 resulting in its removal from the normal, covering relation to the connector cover 126. As set forth above, the indicator 128 will also be detached from the housing 116, due to the directional force applied to the housing, and will become visually exposed by virtue of it remaining attached in surrounding relation the female connector 12' and immediately adjacent the connector cover 126. As a result, the closure assembly 110 of the present invention will provide a clear indication of tampering or attempted access to the female connector 12'.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A closure assembly for a female connector structured to indicate attempted access to the female connector, said closure assembly comprising:
    a housing including an at least partially hollow interior and a closed end portion,
    a connector cover movably disposed within said housing in attachable relation to the female connector, said connector cover including an interior chamber having a surrounding interior surface disposed and dimensioned in receiving, at least partially enclosing relation to an access port of the female connector,
    an indicator member fixedly and removably connected within said housing and detachable there from upon removal of said housing from the female connector,
    said indicator member disposed in surrounding, immediately adjacent relation to said connector cover on an interior of said housing,
    said indicator member retained in said surrounding, immediately adjacent relation to an exterior of said connector cover, upon removal of said housing from said connector cover, when said connector cover is attached to the female connector,
    said surrounding interior surface of said connector cover cooperatively structured with the exterior of the female connector to establish a connection there-between, and
    said connector cover and housing cooperatively structured for concurrent rotation and axial advancement of said interior chamber into said receiving, at least partially enclosing relation to the access port of the female connector.

2. A closure assembly as recited in claim 1 further comprising at least one frangible connector disposed in removable, interconnecting relation between an interior surface of said housing and an exterior surface of said indicator member.

3. A closure assembly as recited in claim 1 comprising a drive assembly disposed on both said closed end portion and a corresponding disposed surface of said connector cover; said closed end portion and said corresponding surface cooperatively structured to facilitate concurrent rotation of said connector cover and said housing in only one direction upon rotation of said housing in said one direction relative to the female connector.

4. A closure assembly as recited in claim 1 wherein said surrounding interior surface comprises a threaded portion disposed and configured to define a threaded engagement of said connector cover to the access port upon said rotation of said housing in said one direction.

5. A closure assembly as recited in claim 1 wherein said interior chamber includes an open end and an oppositely disposed closed end disposed in interconnected relation by said surrounding interior surface; said open end and said closed end being disposed a sufficient spaced distance from one another to receive and enclose at least a majority of the access port of the female connector within said interior chamber.

6. A closure assembly as recited in claim 5 wherein said housing further comprises an open end oppositely disposed to said closed end portion, said housing and said open end thereof being sufficiently dimensioned to receive and surround a remaining portion of the female connector other than the access port.

7. A closure assembly as recited in claim 1 wherein said housing further comprises an open end oppositely disposed to said closed end portion, said housing and said open end thereof being sufficiently dimensioned to receive and surround a remaining portion of the female connector other than the access port.

8. A closure assembly as recited in claim 7 wherein said interior chamber is spaced inwardly from said open end of said housing and disposed to at least partially enclose the access port of the female connector concurrently to said housing surrounding the remaining portion of the female connector.

9. A closure assembly as recited in claim 1 wherein said connector cover includes a casing having an exterior structure at least partially defined by a plurality of curved segments and a plurality of flat segments, each of said plurality of curved and flat segments extending along a length of said casing, each of said flat segments disposed between and adjacent two of said plurality of curved segments.

10. A closure assembly as recited in claim 1 further comprising a disinfecting pad fixedly connected to said connector cover within said interior chamber, said pad including a disinfecting agent contained therein and disposed in engagement with the access port of the female connector to facilitate a disinfecting of at least a portion of the access port, when said connector cover is attached to the female connector.

11. A closure assembly for a female luer connector structured to indicate attempted access to the female connector, said closure assembly comprising:

a housing including an at least partially hollow interior, a closed end portion and an oppositely disposed open end disposed in communicating relation with said hollow interior, an indicator member fixedly and removably connected within said housing and detachable there from, a connector cover movably retained within said housing between said closed end portion and said indicator member, said indicator member disposed in surrounding, immediately adjacent relation to said connector cover on an interior of said housing, said indicator member retained in surrounding, immediately adjacent relation to an exterior of said connector cover, upon removal of said housing from said connector cover, when said connector cover is attached to the female connector, said connector cover including an interior chamber disposed and dimensioned to receive and at least partially enclose an access port of the female connector, said interior chamber of said connector cover including a surrounding interior surface cooperatively disposed and structured with an exterior of the female connector to establish a connection between said connector cover and the female connector, a drive assembly disposed on both said closed end portion and a confronting portion of said connector cover, said drive assembly structured to facilitate concurrent rotation of said connector cover and said housing in only one direction upon rotation of said housing in said one direction relative to the female connector, and said concurrent rotation of said connector cover and said housing at least partially defining rotational and axial movement of said connector cover into said receiving, enclosing relation with the female connector.

12. A closure assembly as recited in claim 11 wherein said drive assembly comprises a first drive segment mounted on said closed end portion and a second drive segment mounted on said confronting portion of said connector cover in engaging relation with said closed end portion.

13. A closure assembly as recited in claim 12 wherein said first and second drive segments are cooperatively structured to rotate said connector cover and said interior chamber in said one direction upon said rotation of said housing in said one direction.

14. A closure assembly as recited in claim 11 wherein said surrounding interior surface of said connector cover is cooperatively structured with the exterior of the female connector to define an axial advancement of said connector cover and said interior chamber into said receiving, at least partially enclosing relation with the access port of the female connector.

15. A closure assembly as recited in claim 14 wherein said surrounding interior surface comprises a threaded portion disposed and configured to define a threaded engagement of said connector cover to the access port upon said rotation of said housing in said one direction.

16. A closure assembly as recited in claim 15 wherein said indicator member is detachable from said housing and retained in said surrounding, immediately adjacent relation to said connector cover upon a predetermined directional force being applied to said housing.

17. A closure assembly as recited in claim 16 wherein said predetermined directional force comprises an axial force sufficient to remove said housing from an interconnected relation to said female connector.

18. A closure assembly as recited in claim 11 wherein said connector cover includes a casing having an exterior structure at least partially defined by a plurality of curved segments and a plurality of flat segments, each of said curved segments and flat segments extending along a length of said casing, each of said flat segments disposed between and adjacent two of said plurality of curved segments.

19. A closure assembly as recited in claim 11 further comprising a disinfecting structure disposed within the interior chamber in cooperative relation to the female connector to facilitate a disinfecting of at least a portion thereof, when said connecting cover and the female connector are connected.

20. A closure assembly as recited in claim 19 wherein said disinfecting structure comprises a pad having a disinfecting agent contained thereon.

21. A closure assembly for a female connector structured to indicate attempted access to the female connector, said closure assembly comprising:

a housing including an at least partially hollow interior and a closed end portion, a connector cover movably disposed within said housing in attachable relation to the female connector, said connector cover including an interior chamber disposed and dimensioned in receiving, at least partially enclosing relation to an access port of the female connector, said connector cover including a casing having an exterior structure comprising a plurality of curved segments and a plurality of flat segments, each of said curved segments and flat segments extending along a length of said casing, each of said flat segments disposed between and adjacent two of said plurality of curved segments, an indicator member fixedly and removably connected within said housing and detachable there from upon removal of said housing from the female connector, and said connector cover and housing cooperatively structured for concurrent rotation and axial movement of said interior chamber into said receiving, at least partially enclosing relation to the access port of the female connector.

22. A tamper evident closure assembly comprising:

a female connector associated with an apparatus for administering intravenous fluids to a patient, a housing including an at least partially hollow interior and a closed the end portion, a connector cover movably disposed within said housing in attachable relation to the female connector, said connector cover including an interior chamber disposed and dimensioned in receiving, at least partially enclosing relation to an access port of the female connector, said interior chamber including a surrounding interior surface cooperatively disposed and structured with an exterior of the female connector to establish a connection between said connector cover and the female connector, an indicator member fixedly and removably connected within said housing and detachable there from upon removal of said housing from said female connector, and said connector cover and said housing cooperatively structured for concurrent rotation and axial movement of said interior chamber into said receiving, at least partially enclosing relation to the access port of said female connector.

* * * * *